(12) United States Patent
Kawatahara et al.

(10) Patent No.: US 7,155,371 B2
(45) Date of Patent: **\*Dec. 26, 2006**

(54) MEASURING DEVICE WITH COMMENT INPUT FUNCTION

(75) Inventors: Masanao Kawatahara, Kyoto (JP); Akinori Kai, Kyoto (JP); Toshihiko Harada, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/364,668

(22) Filed: Feb. 28, 2006

(65) Prior Publication Data

US 2006/0149510 A1 Jul. 6, 2006

Related U.S. Application Data

(63) Continuation of application No. 10/433,201, filed as application No. PCT/JP01/10466 on Nov. 30, 2001, now Pat. No. 7,039,560.

(30) Foreign Application Priority Data

Nov. 30, 2000 (JP) .............................. 2000-403716
Nov. 30, 2000 (JP) .............................. 2000-403717

(51) Int. Cl.
*G06F 19/00* (2006.01)

(52) U.S. Cl. ............... 702/187; 702/176; 702/177; 600/301; 600/319

(58) Field of Classification Search ............. None
See application file for complete search history.

(56) References Cited

U.S. PATENT DOCUMENTS

| 5,342,054 A * | 8/1994 | Chang et al. ............... 473/156 |
|---|---|---|
| 5,502,656 A * | 3/1996 | Fulcher et al. ............... 702/187 |
| 5,805,289 A * | 9/1998 | Corby et al. ................ 356/613 |
| 5,920,317 A * | 7/1999 | McDonald .................... 715/853 |
| 6,080,106 A | 6/2000 | Lloyd et al. |
| 6,099,319 A * | 8/2000 | Zaltman et al. ............. 434/236 |
| 6,222,449 B1 * | 4/2001 | Twining ................ 340/539.11 |
| 6,315,569 B1 * | 11/2001 | Zaltman ..................... 434/236 |
| 6,661,438 B1 * | 12/2003 | Shiraishi et al. ............ 715/835 |
| 6,862,556 B1 * | 3/2005 | Feola et al. ................. 702/187 |
| 6,977,585 B1 * | 12/2005 | Falk et al. ................... 340/506 |
| 7,039,560 B1 * | 5/2006 | Kawatahara et al. ........ 702/187 |
| 7,041,468 B1 * | 5/2006 | Drucker et al. .............. 435/14 |
| 2001/0054961 A1 * | 12/2001 | Twining .................. 340/573.1 |
| 2002/0059257 A1 * | 5/2002 | Matsumura et al. .......... 707/10 |
| 2002/0062210 A1 * | 5/2002 | Hamada ..................... 704/235 |
| 2002/0099457 A1 * | 7/2002 | Fredlund et al. ............. 700/91 |
| 2002/0120201 A1 * | 8/2002 | Chio et al. .................. 600/490 |
| 2003/0080878 A1 * | 5/2003 | Kirmuss .................... 340/936 |

(Continued)

FOREIGN PATENT DOCUMENTS

EP    1 034 734    9/2000

(Continued)

*Primary Examiner*—Patrick J. Assouad
(74) *Attorney, Agent, or Firm*—Hamre, Schumann, Mueller & Larson, P.C.

(57) ABSTRACT

A measuring device (1) has, e.g., a voice input portion (27) for a measurer to input an arbitrary comment at a time of measurement, and it allows a voice recognition portion (28) to recognize the measurer's comment inputted by the voice input portion (27) and also allows a recognition result to be stored in a comment storing portion (43) in correlation with information on date and time, thereby storing conditions or the like of the measurer at the time of measurement, together with the measurement data.

5 Claims, 9 Drawing Sheets

U.S. PATENT DOCUMENTS

| | | | |
|---|---|---|---|
| 2003/0133129 A1* | 7/2003 | Yagi et al. | 356/602 |
| 2003/0176183 A1* | 9/2003 | Drucker et al. | 455/414.1 |
| 2003/0176986 A1* | 9/2003 | Dietsch et al. | 702/150 |
| 2003/0212379 A1* | 11/2003 | Bylund et al. | 604/504 |
| 2003/0233257 A1* | 12/2003 | Matian et al. | 705/3 |
| 2004/0015102 A1* | 1/2004 | Cummings et al. | 600/584 |
| 2004/0039256 A1* | 2/2004 | Kawatahara et al. | 600/300 |
| 2004/0167414 A1* | 8/2004 | Tanabe et al. | 600/500 |
| 2004/0204635 A1* | 10/2004 | Scharf et al. | 600/323 |
| 2005/0239156 A1* | 10/2005 | Drucker et al. | 435/14 |
| 2005/0267780 A1* | 12/2005 | Ray et al. | 705/2 |
| 2005/0277164 A1* | 12/2005 | Drucker et al. | 435/14 |

FOREIGN PATENT DOCUMENTS

| | | |
|---|---|---|
| JP | 7-116127 | 5/1995 |
| JP | 7-303613 | 11/1995 |
| JP | 10-104027 | 4/1998 |
| WO | 00/62660 | 10/2000 |

* cited by examiner

| Date | Time | Measured Value | Comment |
|---|---|---|---|
| 2000.9.15 | 6:15 | 125mg/dl | |
| 2000.9.15 | 6:35 | ——— | 09150635.dat |
| 2000.9.15 | 6:40 | ——— | 09150640.dat |
| 2000.9.15 | 8:32 | 167mg/dl | 09150832.dat |
| 2000.9.15 | 12:21 | 127mg/dl | |
| 2000.9.15 | 12:40 | ——— | 09151240.dat |
| 2000.9.15 | 18:02 | 117mg/dl | |
| 2000.9.15 | 18:26 | ——— | 09151826.dat |
| 2000.9.15 | 20:30 | ——— | 09152030.dat |
| 2000.9.15 | 22:01 | 135mg/dl | |
| 2000.9.16 | 6:04 | 118mg/dl | |
| 2000.9.16 | 6:32 | ——— | 09160632.dat |

| Date | Time | Measured Value | Comment |
|---|---|---|---|
| 2000.9.15 | 6:15 | 125mg/dl | |
| 2000.9.15 | 6:35 | ——— | Insulin 12 unit |
| 2000.9.15 | 6:40 | ——— | Meal |
| 2000.9.15 | 8:32 | 167mg/dl | Overate a little |
| 2000.9.15 | 12:21 | 127mg/dl | |
| 2000.9.15 | 12:40 | ——— | Meal |
| 2000.9.15 | 18:02 | 117mg/dl | |
| 2000.9.15 | 18:26 | ——— | Eating out |
| 2000.9.15 | 20:30 | ——— | Walking for 40 minutes |
| 2000.9.15 | 22:01 | 135mg/dl | |
| 2000.9.15 | 22:01 | | Insulin injection |
| 2000.9.16 | 6:04 | 75mg/dl | |

FIG. 5

| Comment Code | Comment |
|---|---|
| 01 | Meal |
| 02 | Insulin injection |
| 03 | Exercise |

FIG. 6

| Date | Time | Measured Value | Comment |
|---|---|---|---|
| 2000.9.15 | 6:15 | 125mg/dl | |
| 2000.9.15 | 6:35 | ——— | 09150635.dat |
| 2000.9.15 | 6:40 | ——— | 09150640.dat |
| 2000.9.15 | 8:32 | 167mg/dl | 09150832.dat |
| 2000.9.15 | 12:21 | 127mg/dl | |
| 2000.9.15 | 12:40 | ——— | 09151240.dat |
| 2000.9.15 | 18:02 | 117mg/dl | |
| 2000.9.15 | 18:26 | ——— | 09151826.dat |
| 2000.9.15 | 20:30 | ——— | 09152030.dat |
| 2000.9.15 | 22:01 | 135mg/dl | |
| 2000.9.16 | 6:04 | 118mg/dl | |
| 2000.9.16 | 6:32 | ——— | 09160632.dat |

| Date | Time | Measured Value | Comment |
|---|---|---|---|
| 2000.9.15 | 6:15 | 125mg/dl | |
| 2000.9.15 | 6:35 | ——— | Insulin 12 unit |
| 2000.9.15 | 6:40 | ——— | Meal |
| 2000.9.15 | 8:32 | 167mg/dl | Overate a little |
| 2000.9.15 | 12:21 | 127mg/dl | |
| 2000.9.15 | 12:40 | ——— | Meal |
| 2000.9.15 | 18:02 | 117mg/dl | |
| 2000.9.15 | 18:26 | ——— | Eating out |
| 2000.9.15 | 20:30 | ——— | Walking for 40 minutes |
| 2000.9.15 | 22:01 | 135mg/dl | |
| 2000.9.15 | 22:01 | | Insulin injection |
| 2000.9.16 | 6:04 | 75mg/dl | |

FIG. 12

MEASURING DEVICE WITH COMMENT INPUT FUNCTION

CROSS REFERENCE TO RELATED APPLICATIONS

This application is a Continuation of application Ser. No. 10/433,201, filed Aug. 29, 2003, which is a National Stage of PCT/JP01/10466, filed Nov. 30, 2001, now U.S. Pat. No. 7,039,560, which applications are incorporated herein by reference.

TECHNICAL FIELD

The present invention relates to a measuring device with a comment input function that enables inputting of an arbitrary comment regarding a condition at the time of measuring data.

BACKGROUND ART

Recently, the number of patients of life-style related diseases such as hypertension and diabetes has been increasing year by year. Many of the patients of life-style related diseases do not need to be hospitalized, but they visit medical institutions, e.g., once or twice a month for medical checking. Patients at home use measuring devices for home medical care in order to grasp and manage their own conditions, such as sphygmomanometers and compact blood glucose measuring devices.

For example, diabetics measure their blood glucose level with a compact blood glucose measuring device at home in daily living, and record the measurement result in their 'memorandum book' or allow a memory in the device to store the result, so that they are diagnosed by their doctor on the basis of the recorded data when visiting the medical institution.

Such a recent compact measuring device can transmit data to a host computer provided in a medical institution through a telephone line or the like, so that the medical institution can grasp the condition of the patient even if the patient does not come to the medical institution. As a result, the patient can decrease the number of visits to the medical institution.

For example, JP07(1995)-116127 A discloses a home medical care data management device that can register only data the patient needs, among data measured by the patient using the measuring device. Unless an operation for directing registration is conducted, this device will not register data measured by the patient outside a predetermined measurement time or data measured by a third party using the device. Therefore, it can transmit to a medical institution only measurement data that the medical institution needs.

However, it is known that numerical values of examination items relating to the life-style diseases (blood glucose level, blood pressure, urine or the like) will vary depending on the patient's condition, and thus selecting only exclusive data that the patient needs and transmitting the data to a medical institution is insufficient for the medical institution to diagnose the patient. For example, since the blood glucose level may vary depending on meals, exercises, stress, dosage or the like, checking the influences of these factors is essential for validly comprehending the measurement values. It is particularly known that the blood glucose level is influenced greatly by meals. The blood glucose is lowered when the patient is hungry, and increased after meals. For this reason, knowing the condition of the patient at the measurement is necessary for validly determining the measurement data.

A conventional blood glucose measuring device ("GLUCOCARD GT-1650" produced by Arkray, Inc.) has an "after-meal mark" storage function. This function is for allowing the measuring device to store an "after-meal mark" together with measurement data obtained after a meal so as to indicate that the data is obtained after a meal. A series of operation procedures for storing the "after-meal mark" will be explained below.

A blood glucose measuring device enters a mode of setting an "after-meal mark" after a measurement of blood glucose level, so that it displays a measured value on its screen and also blinks an after-meal mark on the upper right of the measured value. If the measurer continues to press the operation button for at least 2 seconds during the after-meal mark is blinking, the after-meal mark turns on and the measurement result is stored as an after-meal measured value in this blood glucose measuring device. The blood glucose measuring device has a "control mark" storing function as well. By pressing the operation button once briefly during the "after-meal mark" is blinking, a display of "CONT" comes on and the measurement result will be stored as a result of measurement of a standard solution for confirming an accuracy of the blood glucose measuring device.

Since only measurement data registered by a patient will be transmitted to a medical institution in the case of the home medical care data management device, the patient may manipulate the measurement data. For example, the patient will not register data in a case the data are abnormal. Even when the abnormal data are transmitted, the medical institution cannot grasp the cause of the abnormal data, and confirmation of the cause should wait until the patient visits the medical institution for a medical procedure. The patient may forget the situation under which the abnormal data are generated in a case that some days have passed after the generation of the abnormal data by the time the patient visits the medical institution, and this will inhibit grasping of the cause of the abnormal data.

Though the blood glucose measuring device can add a meal mark to the measured value so as to indicate that the measured value is obtained after a meal, it has not been possible to obtain detailed information, for example, whether the measured value is obtained immediately after a meal or after one hour.

It is effective in a medical practice to record times of occurrence of events that will affect the measurement data, for example, times of procedures such as "insulin injection" other than the meal times. However, conventional devices have no functions of storing them. Though in designing the device it is possible to provide various event informations such as storing "control mark" to the measurement result, this will complicate the button operations, so that the operations will be cumbersome for the patient who performs the measurement.

An object of the present invention is to provide a measuring device with a comment input function, which enables storage of an arbitrary comment with simple operations.

DISCLOSURE OF INVENTION

For achieving the above-described object, a measuring device according to the present invention has a measuring portion, a measurement data storing portion for storing measurement data measured by the measuring portion, a comment inputting portion for inputting an arbitrary comment as a voice or an image, a comment recognizing portion for converting the comment inputted by the comment inputting portion into comment data, and a comment storing portion for storing the comment data.

Thereby, a measurer can allow the measuring device to store, together with the measurement data, an arbitrary comment relating to a condition at the time of the measurement. For a case of a measuring device such as a blood glucose measuring device concerning bionics information, it is possible to input as a comment of the patient's condition at the time of measurement, e.g., how many hours have passed from the meal by the time of the measurement. For a case of a measuring device concerning environmental data such as water quality, noises, and atmospheric pollution level, information obtained through the five senses of the measurer may be inputted as a comment. Thereby, in the case of subsequent confirmation of the measurement data, it is possible to know from the comment about under which condition the measurement data were obtained, and this is helpful in analyzing the measurement data. In addition, since the comment input is conducted by using a voice or an image, an operator of the measuring device is not required to conduct any complicated operations.

BRIEF DESCRIPTION OF DRAWINGS

FIG. 5 shows an example of comment data outputted as a text in a measuring device with a comment input function according to the first embodiment.

FIG. 6 shows a relationship between event codes and comments.

FIG. 12 shows an example of comment data outputted as a text in the measuring device with a comment input function according to the second embodiment.

PREFERRED EMBODIMENT OF THE INVENTION

Hereinafter, embodiments of the present invention are described with reference to the attached drawings.

(First Embodiment)

Figure 1:
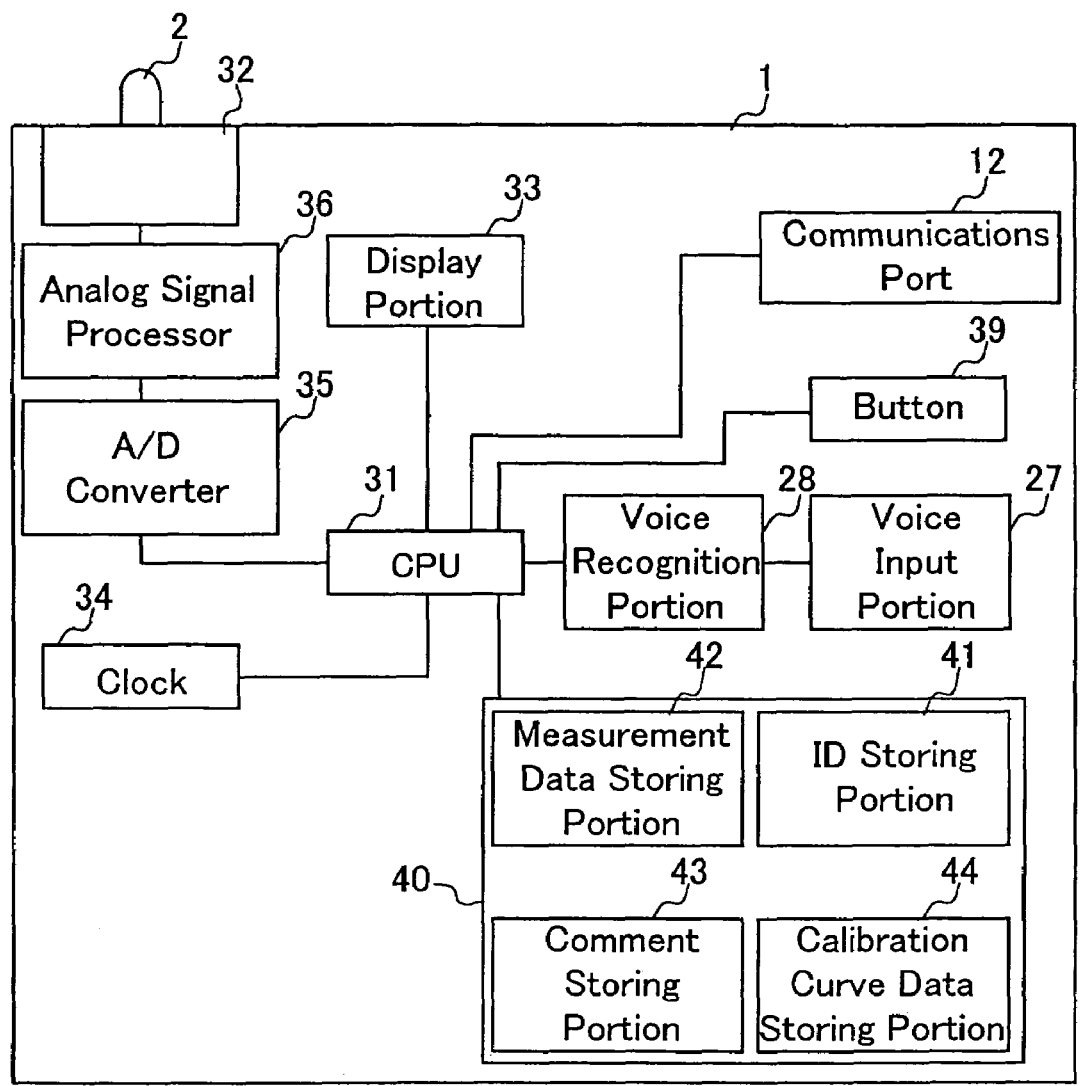
FIG. 1 is a block diagram showing a first embodiment of a measuring device with a comment input function according to the present invention.

FIG. 1 is a block diagram showing an internal configuration of a compact blood glucose measuring device according to a first embodiment of the present invention. The compact blood glucose measuring device 1 is provided with a CPU 31 serving as a controlling portion, to which are connected a storing portion 40, a display portion 33, a clock 34, a sensor insertion portion 32 for accepting a sensor 2, an analog signal processor 36 for amplifying an output signal from the sensor 2, an A/D converter 35 for converting an output signal from the analog signal processor 36 to a digital signal, a communications port 12 for performing transmission and reception of data with the outside, a voice input portion 27 for inputting voice information from the outside, and a voice recognition portion 28 for recognizing an inputted voice. Furthermore, the storing portion 40 includes an ID storing portion 41, a measurement data storing portion 42, a comment storing portion 43, and a calibration curve data storing portion 44.

Figure 2:
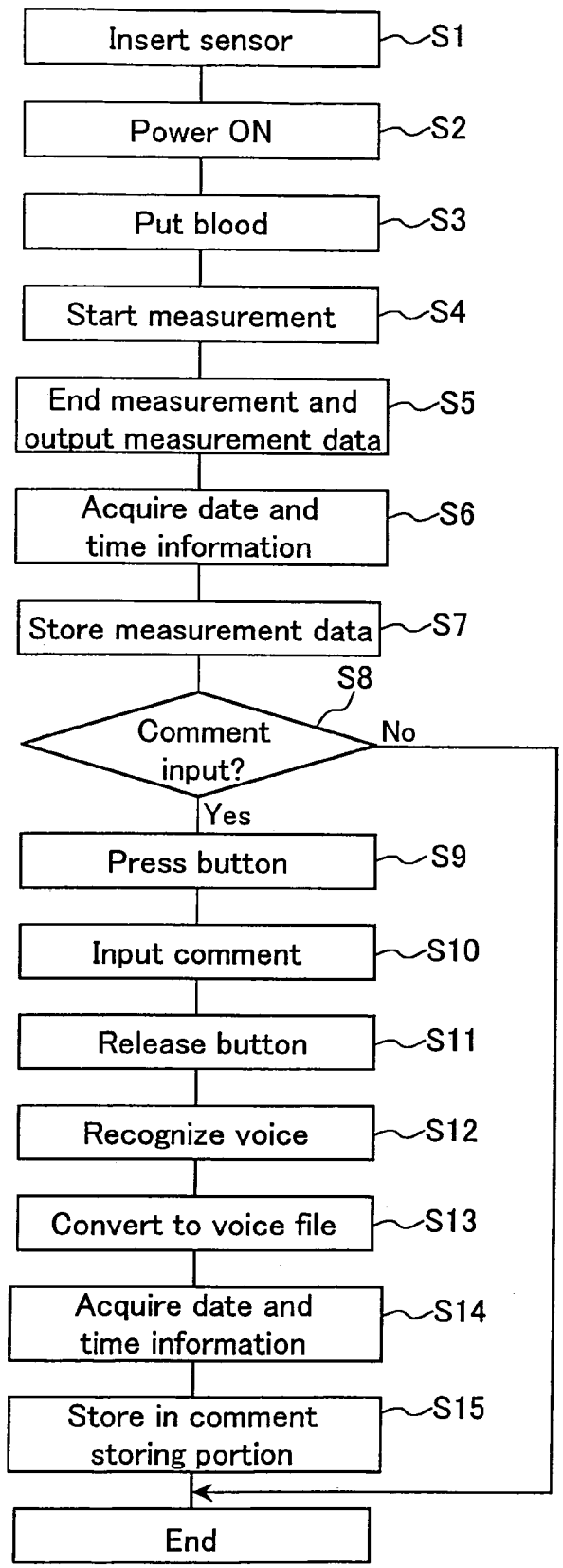
FIG. 2 is a flow chart showing a processing procedure from measurement to comment input.

A procedure of a measurement using the compact blood glucose measuring device 1 of the above-described configuration will be explained below with reference to FIG. 2. A patient inserts the sensor 2 into the sensor insertion portion 32 of the compact blood glucose measuring device 1 (S1 in FIG. 2). By inserting the sensor 2 into the sensor insertion portion 32, the compact blood glucose measuring device 1 is turned on (S2). Subsequently, the compact blood glucose measuring device 1 enters a measurement standby state.

The patient pricks his fingertip with a needle-like element to collect his blood. When the patient contacts a tip of the sensor 2 attached to the compact blood glucose measuring device 1 with the collected blood, the blood is absorbed into the sensor 2 (S3). When an electrode (not shown) of the sensor 2 detects the blood, the compact blood glucose measuring device 1 starts measurement (S4). After a predetermined amount of time has passed from the start of the measurement, the output from the sensor 2 is amplified by the analog signal processor 36, converted into a digital signal by the A/D converter 35, and sent to the CPU 31 (S5). The CPU 31 refers to the calibration curve data stored in the calibration curve data storing portion 44 of the storing portion 40, converts the sensor output value into a component concentration, displays on the display portion 33 the concentration value as measurement data, and at the same time, it obtains data and time information from the clock 34 (S6), correlates the obtained date and time information with the measurement data, and stores the information and the data in the measurement data storing portion 42 (S7).

Next, the compact blood glucose measuring device 1 displays on the display portion 33 a message of "Comment input?" (S8). For inputting a comment, the patient speaks his comments such as "I overate a little" toward the voice inputting portion 27 while pressing a button 39 of the compact blood glucose measuring device 1, and releases the button 39 when the speech is over (S9–S11).

Voice information inputted through the voice inputting portion 27 is recognized by the voice recognition portion 28 (S12), converted into a voice data file (S13), and stored (S15) in the comment storing portion 43 together with date and time information acquired (S14) from the clock 34 by the CPU 31. Regarding the voice recognition in S12, a voice is recognized, for example, based on the short time pattern change of the frequency component in the voice by using a pattern recognition method, a matching method or the like.

When the comment input is conducted within 1 minute from the measurement, the inputted comment is stored in the comment storing portion 43 in correlation with measurement data stored as a result of the measurement in the measurement data storing portion 42. After a certain amount of time has passed from the measurement, the compact blood glucose measuring device 1 is turned off automatically.

The correlation between the measurement data stored in the measurement data storing portion 42 and the comment to be stored in the comment storing portion 43 may not be explicit necessarily. For example, at a time of storing measurement data and a comment, any explicit correlation will not be provided between them. Instead, when transmitting measurement data from the compact blood glucose measuring device 1 to the outside as described below, the date and time information of the measurement data is compared with the date and time information of the comment. When the difference between them is within one minute, the measurement data and the comment can be regarded as being correlated with each other.

In addition, in the compact blood glucose measuring device 1 according to this embodiment, comment input can be conducted alone regardless measurement of data. A procedure for a case of conducting comment input alone is as follows. First, a patient presses the button 39 of the compact blood glucose measuring device 1 so that the compact blood glucose measuring device 1 is turned on. The patient speaks his comments such as "Meal" and "Insulin 12 units" while pressing the button 39, and releases the button 39 when the speech is over. The voice information inputted through the voice input portion 27 is recognized by the voice recognition portion 28, correlated with date and time information obtained from the clock 34, and stored as a voice data file in the comment storing portion 43.

The next description is about a procedure for a case of conducting transmission of measurement data from the compact blood glucose measuring device 1 to an external device. When the power is on by pressing the button 39 under a condition that a communications cable (not shown) is connected to the communications port 12, the compact blood glucose measuring device 1 starts up in the communications mode. When pressing the button 39 once more, the measurement data stored in the measurement data storing portion 42 of the storing portion 40 and also comment data stored in the comment storing portion 43 are transmitted from the communications port 12 in a time order. The external device to which the data are to be transmitted can be a data management device such as a personal computer that the patient has, or it can be a data management device for a medical institution or the like, which is connected directly to the compact blood glucose measuring device 1 through a modem and a public line.

Figures 3, 4:
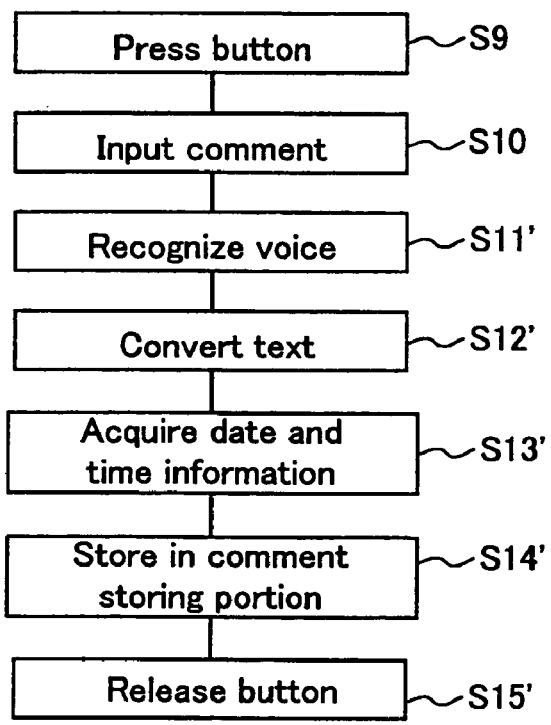
FIG. 3 shows comment data outputted as a voice information file.
FIG. 4 is a flow chart showing a processing procedure for converting voice information into text data.

FIG. 3 shows an example of data transmitted to an external device. As shown in FIG. 3, data to be transmitted to an external device are composed of a unit of a record including 4 items of date, time, measured value and a comment file. A comment stored in correlation with the measurement data is transmitted as a series of data, i.e., as a record identical to the measurement data. Data including comment data alone will be transmitted, indicating the measurement data as "_____".

In the data example of FIG. 3, for example, data having date and time information of "6:15" of "Sep. 15, 2000" denote measurement data stored alone in the measurement data storing portion 42 without any correlation with comments. Data having date and time information of "6:35" of the same date denote a comment stored alone in the comment storing portion 43 without any correlation with the measurement data. On the other hand, data having date and time information of "8:32" of the same date denote data stored in the storing portion 40 as a series of data of correlated measurement data and a comment. Here, the date and time information of this series of data are acquired as date and time information of the measurement data in S6 of FIG. 2.

In the above-described embodiment, the comment data denote data stored in a file as voice information. Alternatively, the data can be converted into text data so as to be stored and transmitted. In this case, the processes of S9–S15 in the flow chart of FIG. 2 are replaced by the processes of S9–S15' shown in FIG. 4. That is, an inputted voice is recognized by the voice recognition portion 28 (S11'), the recognized voice information is converted into text information (S12'), and the converted text data are stored with date and time information in the comment storing portion 43 (S13'–S14'). The patient releases the button (S15') when the comment input is over. Even for this case of converting a comment into text data and storing it, the procedure of transmitting measurement data from the compact blood glucose measuring device 1 to the external device is the same as the above-mentioned case of converting a comment into a file as voice information, except for transmitting not a comment file but a comment converted into text data.

Alternatively, the comment data can be stored after being converted into an event code that has been set. The event code denotes a code that a patient attaches originally to each of behaviors or the like that he plans to include in the comments. For example, "meal" and "insulin injection" are set previously as event codes "01" and "02". When a voice of "I am just having a meal" is inputted, a term of "meal" is extracted from voice information and stored as an event code "01" in the comment storing portion 43. When a comment of "I Injected insulin" is inputted as a voice, a term of "Insulin injection" is extracted from voice information and stored as an event code "02" in the comment storing portion 43. Similarly in this case, a procedure for transmitting the measurement data from the compact blood glucose measuring device 1 to the external device is the same as the above-described case where the comment is converted to a file as voice information, except for transmitting not a comment file but a comment converted into an event code. In this case, the event code and the comment are stored in association with each other in a data management device at the receiver side as well, and thus, for outputting the data, the event code "01" is inverted into "meal" and outputted, while the event code "02" is inverted into "insulin injection" and outputted.

As described above, by converting a patient's comment into text data or an event code and storing, the storage capacity of the comment storing portion 43 can be used effectively. Similarly, when transmitting measurement data and comments to the external device, the volume of the transmission data can be reduced in comparison with a case of transmitting the comment as it is, thereby improving the transmission efficiency.

Though this embodiment is explained in a relationship with a compact blood glucose measuring device, the present invention will not be limited to such a compact blood glucose measuring device, but it can be applied to any arbitrary measuring devices such as an electrocardiograph and a sphygmomanometer.

(Second Embodiment)

Another embodiment of the present invention is described with reference to the attached drawings.

Figure 7:
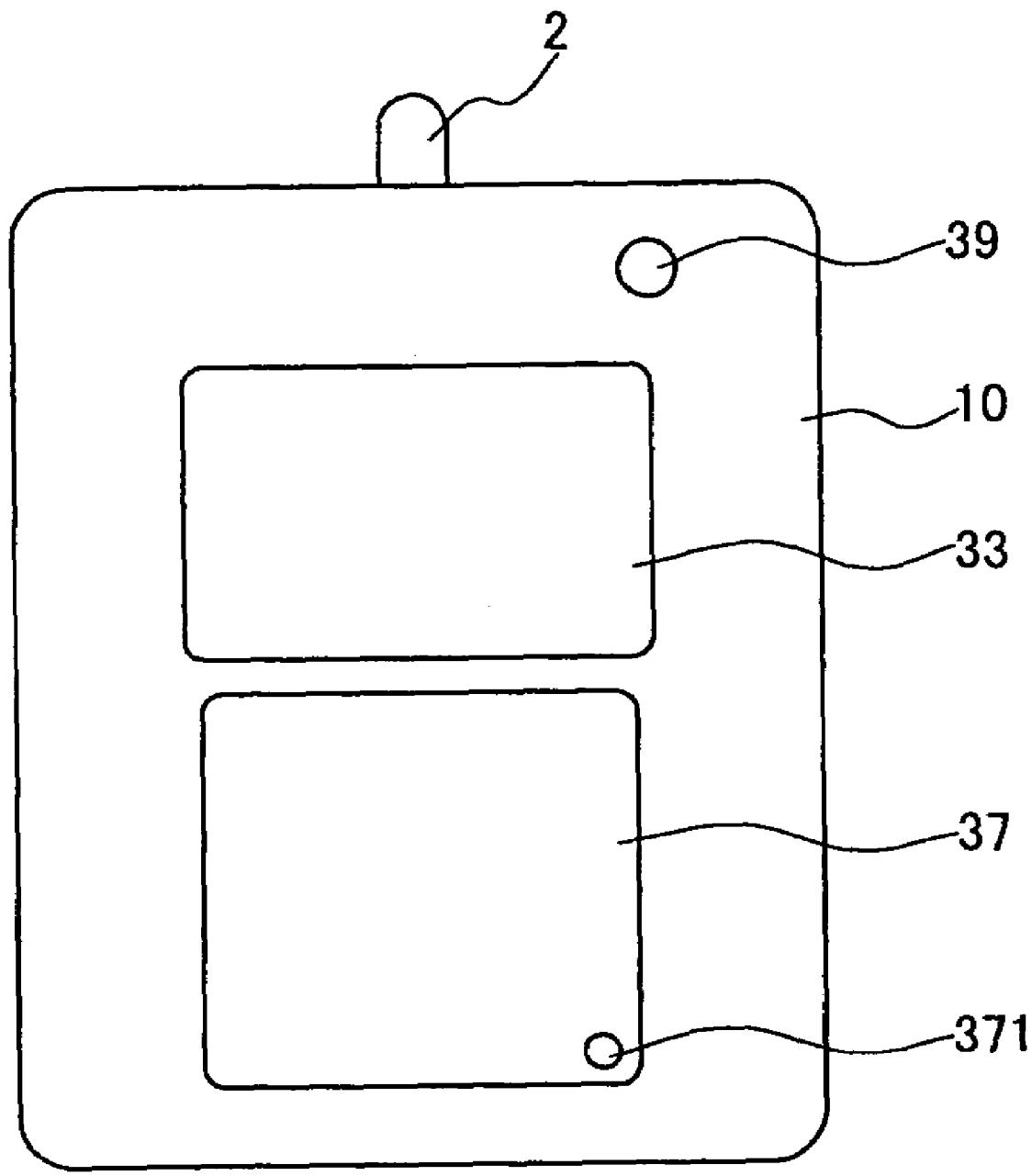
FIG. 7 is a front view showing a second embodiment of a measuring device with a comment input function according to the present invention.

FIG. 7 is a front view of a compact blood glucose measuring device 10 according to a second embodiment of the present invention. As shown in FIG. 7, in the front face of the compact blood glucose measuring device 10, are provided a display portion 33 for displaying measurement results or the like, a pen-input portion 37 for inputting character information or the like, and a button 39 for operation. The numeral 371 in FIG. 7 denotes an input ending button provided in the pen-input portion 37.

While FIG. 7 shows an example of a configuration in which the display portion and the pen-input portion are formed separately, the display portion and the pen-inputting portion can be formed integrally by using a touch panel or the like as a combination of a liquid crystal display panel and a pressure sensitive element.

Figure 8:
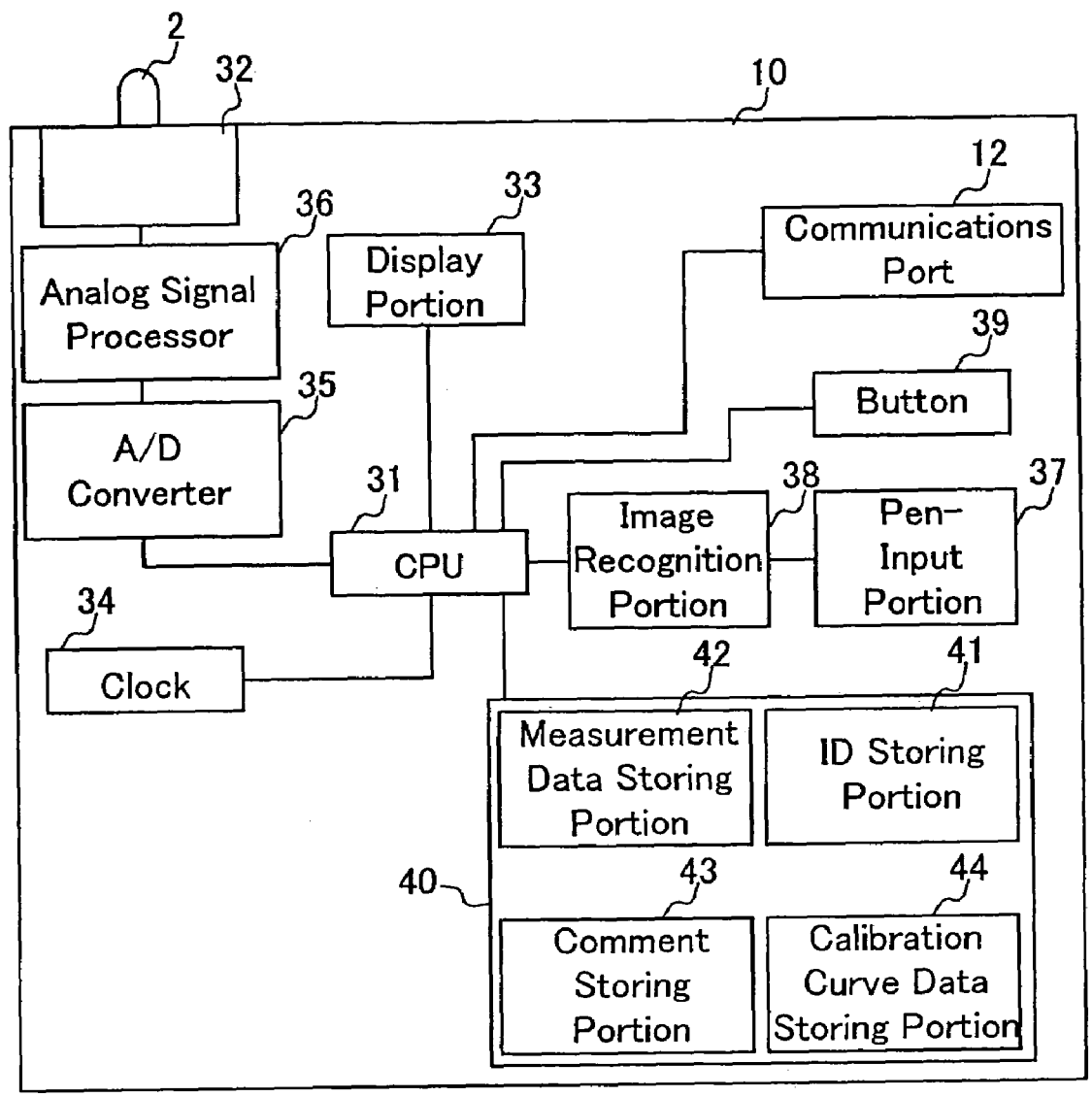
FIG. 8 is a block diagram of a measuring device with a comment input function according to the second embodiment.

FIG. 8 is a block diagram showing an internal configuration of a compact blood glucose measuring device according to this embodiment of the present invention. The compact blood glucose measuring device 10 is provided with a CPU 31 serving as a controlling portion, to which are connected a storing portion 40, a display portion 33, a clock 34, a sensor insertion portion 32 for accepting a sensor 2, an analog signal processor 36 for amplifying an output signal from the sensor 2, an A/D converter 35 for converting an output signal from the analog signal processor 36 to a digital signal, a communications port 12 for performing transmission and reception of data with the outside, a pen-input portion 37 for inputting image information such as handwritten characters from the outside, and an image recognition portion 38 for recognizing inputted image information. The storing portion 40 includes an ID storing portion 41, a measurement data storing portion 42, a comment storing portion 43, and a calibration curve data storing portion 44.

Figure 9:
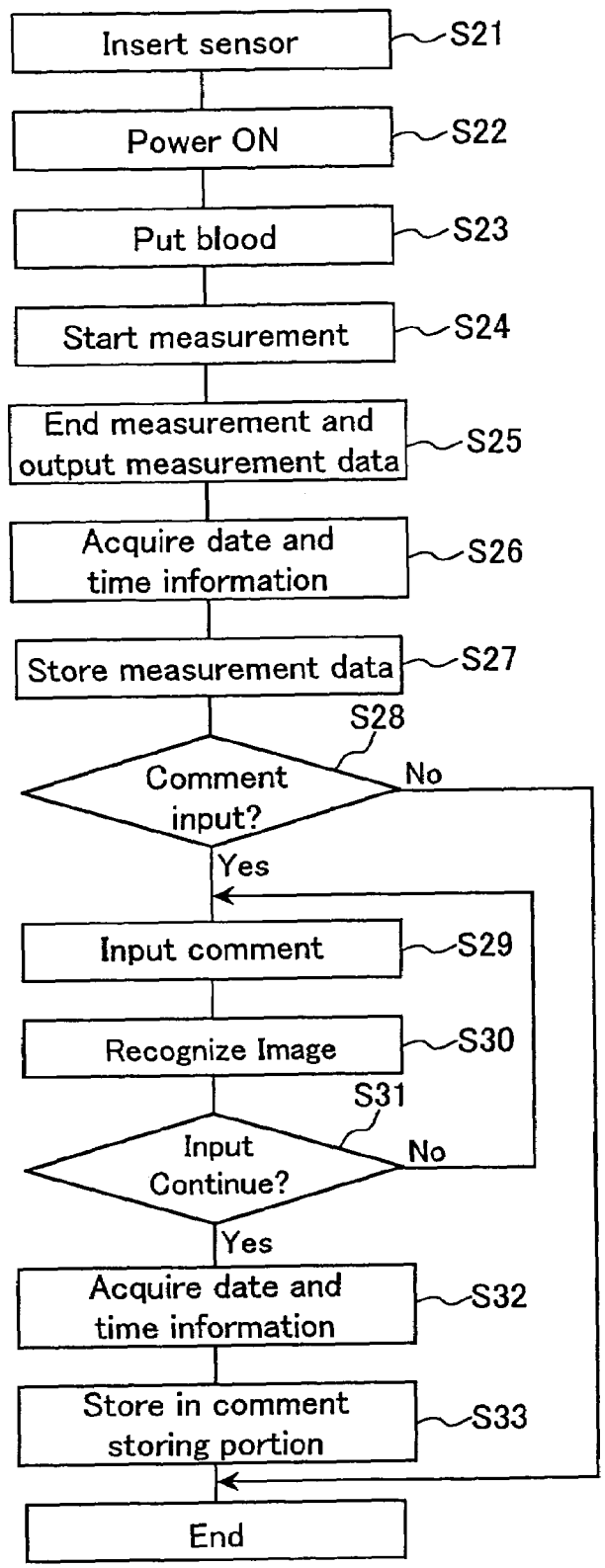
FIG. 9 is a flow chart showing a processing procedure from measurement to comment inputting in the measuring device with a comment input function according to the second embodiment.

A procedure of a measurement using the compact blood glucose measuring device 10 of the above-described configuration will be explained below with reference to FIG. 9. A patient inserts the sensor 2 into the sensor insertion portion 32 of the compact blood glucose measuring device 10 (S21 in FIG. 9). By inserting the sensor 2 into the sensor insertion portion 32, the compact blood glucose measuring device 10 is turned on (S22). Subsequently, the compact blood glucose measuring device 10 enters a measurement standby state.

The patient pricks his fingertip with a needle-like element to collect his blood. When the patient contacts a tip of the sensor 2 attached to the compact blood glucose measuring device 10 with the collected blood, the blood is absorbed into the sensor 2 (S23). When an electrode (not shown) of the sensor 2 detects the blood, the compact blood glucose measuring device 10 starts measurement (S24). After a predetermined amount of time has passed from the start of the measurement, the output from the sensor 2 is amplified by the analog signal processor 36, converted into a digital signal by the A/D converter 35, and sent to the CPU 31 (S25). The CPU 31 refers to the calibration curve data stored in the calibration curve data storing portion 44 of the storing portion 40, converts the sensor output value into a component concentration and displays on the display portion 33 the concentration value as measurement data. At the same time, it obtains data and time information from the clock 34 (S26), correlates the obtained date and time information with the measurement data, and stores the information and the data in the measurement data storing portion 42 (S27).

Next, the compact blood glucose measuring device 10 displays on the display portion 33 a message of "Comment input?" (S28). For inputting a comment, the patient inputs by a handwriting his comment such as "I overate a little" by using a pen (not shown) with respect to the pen-input portion 37 of the compact blood glucose measuring device 10 (S29). The pen chirography inputted into the pen-input portion 37 is displayed on the display portion 33. Namely, the patient can conduct the input while watching the image displayed on the display portion 33 so as to check the characters being inputted.

When there is no input for a predetermined period after a series of input, the image recognition portion 38 recognizes the series of input as one character (S30). After recognition of a character, the image on the display portion 33 is cleared to provide a standby state for the next input (S31). When the input of all comments to be inputted is over, the patient touches with the pen the input ending button 371 (see FIG. 7) located on the lower right of the pen-input portion 37. Thereby, comment input is over. The image (character) recognition by means of the image recognition portion 38 can be conducted, for example, by using a pattern matching method, a sonde method, or the like.

When the comment input is over, the image information recognized in S30 is converted into an image data file, and stored (S33), in the comment storing portion 43, with a date and time information (S32) acquired from the clock 34 by the CPU 31. When the comment input is conducted within 1 minute from the measurement, the inputted comment is stored in the comment storing portion 43 in correlation with measurement data stored as a result of the measurement in the measurement storing portion 42. After a certain amount of time has passed from the measurement, the compact blood glucose measuring device 1 is turned off automatically.

The correlation of the measurement data stored in the measurement data storing portion 42 and the comment to be stored in the comment storing portion 43 may not be explicit necessarily. For example, at a time of storing measurement data and a comment, any explicit correlation will not be provided between them. Instead, when transmitting measurement data from the compact blood glucose measuring device 10 to the outside as described below, the date and time information of the measurement data is compared with the date and time information of the comment. When the difference between them is within one minute, the measurement data and the comment can be regarded as being correlated with each other.

In addition, in the compact blood glucose measuring device 10 according to this embodiment, comment inputting can be conducted alone regardless of the measurement of data. A procedure for a case of conducting comment input alone is as follows. First, a patient presses the button 39 of the compact blood glucose measuring device 10 so that the compact blood glucose measuring device 10 is turned on. Using a pen, the patient inputs by handwriting his comments such as "Meal" and "Insulin 12 units" with regard to the pen-input portion 37. The image information inputted through the pen-input portion 37 is recognized by the image recognition portion 38, and stored as an image data file in the comment storing portion 43 in correlation with the date and time information obtained from the clock 34.

The following description is about a procedure for a case of conducting transmission of measurement data from the compact blood glucose measuring device 10 to an external device. When the power is on by pressing the button 39 under a condition that a communications cable (not shown) is connected to the communications port 12, the compact blood glucose measuring device 10 starts up in the communications mode. When pressing the button 39 once more, the measurement data stored in the measurement data storing portion 42 of the storing portion 40 and also comment data stored in the comment storing portion 43 are transmitted from the communications port 12 in a time order. The external device to which the data are to be transmitted can be a data management device such as a personal computer a patient has, or it can be a data management device for a medical institution or the like, which is connected directly to the compact blood glucose measuring device 10 through a modem and a public line.

Figures 10, 11:
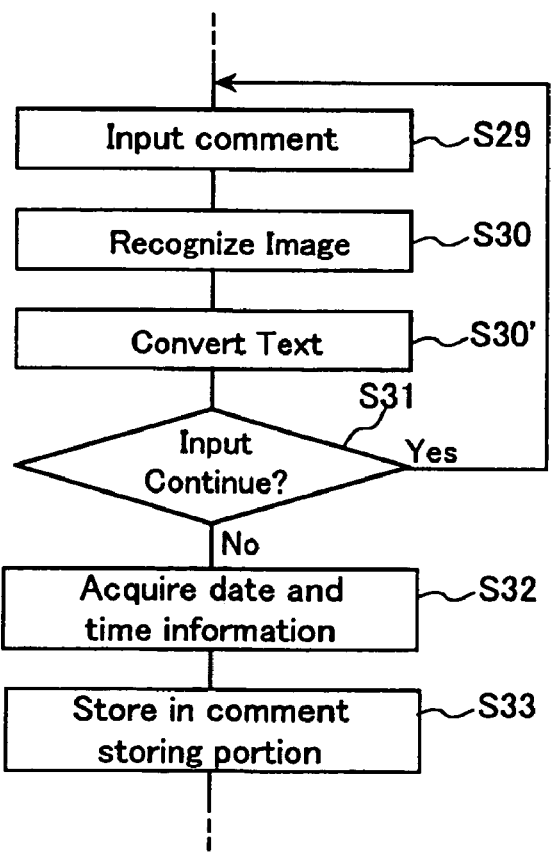
FIG. 10 is a flow chart showing a processing procedure for converting voice information into text data in the measuring device with a comment input function according to the second embodiment.
FIG. 11 is a flow chart showing a processing procedure for converting image information into text data in the measuring device with a comment input function according to the second embodiment.

FIG. 10 shows an example of data transmitted to an external device. As shown in FIG. 10, data to be transmitted to an external device are composed of a unit of a record including 4 items of date, time, measured value and a comment file. A comment stored in correlation with the measurement data is transmitted as a series of data, i.e., as a record identical to the measurement-data. Data including comment data alone will be transmitted, indicating the measurement data as "_____".

In the data example of FIG. 10, for example, data having date and time information of "6:15" of "Sep. 15, 2000" denote measurement data stored alone in the measurement data storing portion 42 without any correlation with a comment. Data having date and time information of "6:35" of the same date denote a comment stored alone in the comment storing portion 43 without any correlation with the measurement data. On the other hand, data having date and time information of "8:32" of the same date denote data stored in the storing portion 40 as a series of data of correlated measurement data and a comment. Here, the date and time information of this series of data are acquired as date and time information of the measurement data in S26 of FIG. 9.

Here, the comment data are converted into a file as image information. Alternatively, the data can be converted into text data so as to be stored and transmitted. In this case, subsequent to S30 in the flow chart shown in FIG. 9, a process (S30') for converting the image information recognized in the image recognition portion 38 into text information is added as shown in FIG. 11, and the converted text data are stored in the comment storing portion 43. Similarly in this case, the procedure for transmitting measurement data from the compact blood glucose measuring device 10 to the outside is the same as the above-described case where the comment is converted into a file as image information, except for transmitting not an image data file of a comment but a comment converted into text data.

Alternatively, the comment data can be stored after being converted into an event code that has been set. In this case, "meal" and "insulin injection" are set previously so as to be stored as event codes "01" and "02". For example, when a comment including words of "at meal" is inputted, a term of "meal" is extracted from this comment and stored as an event code "01" in the comment storing portion 43. When a comment of "Injected insulin" is inputted, a term of "Insulin injection" is extracted from this comment and stored as an event code "02" in the comment storing portion 43. Similarly in this case, a procedure for transmitting the measurement data from the compact blood glucose measuring device 10 to the external device is the same as the above-described case where the comment is converted to a file as voice information, except for transmitting not a comment file but a comment converted into an event code. In this case, the event code and the comment are stored in a data management device at the receiver side as well in a correlated state, and thus, for outputting the data, the event code "01" is inverted into "meal" and outputted, while the event code "02" is inverted into "insulin injection" and outputted.

As described above, by converting a patient's comment into text data or an event code and storing, the storage capacity of the comment storing portion 43 can be used effectively. Similarly, when transmitting measurement data and comments to the external device, the volume of the transmission data can be reduced in comparison with a case of transmitting the comment as it is, thereby improving the transmission efficiency.

While the above-described first and second embodiments show measuring devices, each of which has a measuring portion and a comment inputting portion assembled in a housing, a measuring device composed of plural pieces of hardware is included also in the scope of the present invention. The present invention includes, for example, forming a voice input device or an image input device as a comment inputting portion, which will be a piece of hardware separated from a device having a measurement sensor or the like, and connecting either the voice input device or the image input device through a cable (or it can be a wireless connection through an infrared ray or the like) for use in a case of comment input. Though this embodiment refers to a configuration of inputting comments by handwriting, it is also possible to key-input comments by using a keyboard or the like, and to store and transmit the inputted comment as text data.

Each of the above embodiments in the present invention is described by referring to a compact blood glucose measuring device. The present invention is not limited to such a compact blood glucose measuring device, but it can be applied to arbitrary measuring devices such as electrocardiographs or sphygmomanometers. In addition, the present invention is not limited to measuring devices for medical use, but it can be applied also to, e.g., devices for measuring environmental data such as water quality, soil, and atmospheric constituents, and any other measuring devices for arbitrary uses.

INDUSTRIAL APPLICABILITY

As mentioned above, the present invention can provide a measuring device that enables inputting comments on measurement data by a simple operation and correlating the measurement data and the comment for transmission to an external device. Thereby, for example, a background of abnormal data can be grasped before a diagnosis of a patient, resulting in an effective medical practice. Furthermore, as a patient can input comments into the measurement data in a simple manner when abnormal data are generated, he will consider what has caused the abnormal data. As a result, the patient will be interested in self-control in his daily life, and thus succeed in managing his own condition.

The invention claimed is:

1. A measuring device with a comment input function, the measuring device comprising:
   a measuring portion,
   a measurement data storing portion for storing measurement data measured with the measuring portion,
   a comment inputting portion for inputting an arbitrary comment as a voice or an image,
   a comment recognizing portion for converting a comment inputted by the comment inputting portion into comment data,
   a comment storing portion for storing the comment data, and
   a date and time information acquiring portion for acquiring date and time information;
   when a time interval between measurement date and time acquired by the date and time information acquiring portion and date and time of the comment input is within a predetermined range, the measurement data and the comment data are correlated with each other and stored in the measurement data storing portion and in the comment storing portion.

2. The measuring device with a comment input function according to claim 1, wherein the comment inputting portion inputs the comment as a voice, and the comment recognizing portion converts the comment inputted by the comment inputting portion into voice data to be stored in the comment recognizing portion.

3. The measuring device with a comment input function according to claim 1, wherein the comment inputting portion inputs the comment as an image, and the comment recognizing portion converts the comment inputted by the comment inputting portion into image data to be stored in the comment recognizing portion.

4. The measuring device with a comment input function according to claim 1, wherein the comment recognizing portion converts the comment inputted by the comment inputting portion into text data.

5. The measuring device with a comment input function according to claim 1, wherein the comment recognizing portion converts the comment inputted by the comment inputting portion into an event code.

* * * * *